(12) United States Patent
Metzger et al.

(10) Patent No.: US 7,407,519 B2
(45) Date of Patent: Aug. 5, 2008

(54) PROCESS FOR IMPROVING THE SUN PROTECTION FACTOR OF CELLULOSIC FIBRE MATERIAL

(75) Inventors: Georges Metzger, Moernach (FR); Fabienne Cuesta, Waldighoffen (FR)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/650,009

(22) Filed: Jan. 5, 2007

(65) Prior Publication Data

US 2007/0107137 A1    May 17, 2007

Related U.S. Application Data

(63) Continuation of application No. 10/507,954, filed as application No. PCT/EP03/02440 on Mar. 10, 2003, now abandoned.

(30) Foreign Application Priority Data

Mar. 18, 2002   (EP)   ................... 02405205

(51) Int. Cl.
    *D06L 3/12*   (2006.01)
(52) U.S. Cl. ............ 8/648; 8/115.51; 8/115.6; 8/116.1
(58) Field of Classification Search ........ 8/115.51, 8/648, 115.6, 116.1
    See application file for complete search history.

(56) References Cited

U.S. PATENT DOCUMENTS

| 5,700,295 A | | 12/1997 | Fuso et al. ................ 8/189 |
| 5,744,599 A | * | 4/1998 | Reinehr et al. ............ 544/193.1 |
| 5,800,862 A | * | 9/1998 | Kaufmann et al. .......... 427/158 |

2003/0192137 A1    10/2003   Cuesta et al. ............... 8/518

FOREIGN PATENT DOCUMENTS

| CH | 640899 | | 1/1984 |
| DE | 2335570 | | 1/1974 |
| EP | 0922699 | | 6/1999 |
| WO | 01/19804 | | 3/2001 |
| WO | 02/08511 | * | 1/2002 |

OTHER PUBLICATIONS

Chemical Abstract 1984:193483 for CH 640899 (Jan. 1984).
Chemical Abstract 1974-146982 for DE 2335570 (Jan. 1974).

* cited by examiner

*Primary Examiner*—Lorna M. Douyon
*Assistant Examiner*—Amina Khan
(74) *Attorney, Agent, or Firm*—Tyler A. Stevenson

(57) ABSTRACT

A process for improving the sun protection factor (SPF) of cellulosic fibre materials and blends thereof, which comprises contacting said materials with at least one compound of the formula (1)

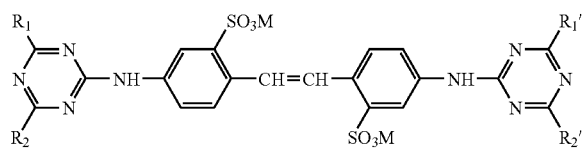

(1)

in which M is hydrogen, an alkali metal atom, ammonium or a cation formed from an amine; $R_1$ and $R_1'$ independently of each other are $-NH-R_3$, $-N(R_3)_2$ or $-O-R_3$, wherein $R_3$ is aryl substituted by $-CO-X-R_5$, wherein X is O or NH and $R_5$ is optionally substituted $C_1$-$C_4$-alkyl, $R_2$ is a group of formula $-O-R_4$ wherein $R_4$ is hydroxy alkyl, alkoxy alkyl or hydroxy alkoxy alkyl,
and $R_2'$ has the meaning of $R_1$ or $R_2$.

13 Claims, No Drawings

PROCESS FOR IMPROVING THE SUN PROTECTION FACTOR OF CELLULOSIC FIBRE MATERIAL

This application is a continuation of application Ser. No. 10/507,954, filed Sep. 14, 2004 abandoned, which is a 371 of PCT/EP 03/02440, filed Mar. 10, 2003, the contents of which are incorporated by reference.

The present invention relates to a process for improving the sun protection factor (SPF) of cellulosic fibre materials and blends thereof, which comprises treating the cellulosic fibre materials with at least one fluorescent whitening agent (FWA). The invention moreover relates to new fluorescent whitening agents useful for that process.

The skin-damaging effect of UV radiation is well known. Protection from strong sunlight is usually sought by applying a sun cream, a composition that contains a UV absorber, directly to the skin. In particularly sunny regions, for example in Australia or America, however, the rate of skin damage due to UV radiation has recently been increasing dramatically. Accordingly, more attention is paid in these countries to protecting the skin from solar irradiation.

It has therefore been proposed that the skin should be protected not just directly, but also to reduce the UV transmissibility of the clothing and also of other sun protection articles, such as awnings or parasols. Especially cellulosic fibre materials are at least partially transparent to UV radiation, so that the mere wearing of clothing does not offer adequate protection to the skin from damage due to UV radiation. A remedy is possible here by incorporating UV absorbers and/or FWA's into the fibre material.

However, hitherto the results achieved in respect of the protection from UV radiation in the area of cellulosic fibre materials, in particular textile materials have not been completely satisfactory and there therefore continues to be a need for improving the sun protection factor of these materials.

It has now been found that, surprisingly, a particular class of fluorescent whitening agents not only provides excellent sun protection factors for cellulosic fibre materials in general, but also results in little or no observable reduction of the degrees of whiteness of the so-treated materials.

Correspondingly, the present invention provides a process for improving the sun protection factor (SPF) of cellulosic fibre materials and blends thereof, which comprises contacting said materials with at least one compound of the formula

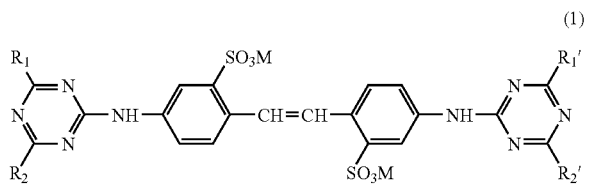

(1)

in which M is hydrogen, an alkali metal atom, ammonium or a cation formed from an amine; $R_1$ and $R_1'$ independently of each other are $-NH-R_3$, $-N(R_3)_2$ or $-O-R_3$, wherein $R_3$ is aryl substituted by $-CO-X-R_5$, wherein X is O or NH and $R_5$ is optionally substituted $C_1$-$C_4$-alkyl, $R_2$ is a group of formula $-O-R_4$ wherein $R_4$ is hydroxy alkyl, alkoxy alkyl or hydroxy alkoxy alkyl, and $R_2'$ has the meaning of $R_1$ or $R_2$.

$R_2$ and $R_2'$ can have different meanings. Preferably, however, they are identical.

According to the invention, alkyl radicals are to be understood as being generally open-chain or branched alkyl radicals containing from 1 to 6 carbon atoms, for example methyl, ethyl, n- or iso-propyl, n-, sec- or tert-butyl or n-hexyl, n-octyl. Cycloalkyl is preferably cyclopentyl or cyclohexyl.

These alkyl groups can be substituted, e.g. by $C_1$-$C_4$ alkoxy or hydroxy.

$R_3$ as aryl is preferably independently of each other phenyl or naphthyl.

In preferably used compounds of formula (1) $R_1$ and $R_1'$ are identical and especially preferred is the use of a compound of formula (1), wherein $R_1$ and $R_1'$ are each $-NH-R_3$, $-N(R_3)_2$ or $-O-R_3$, wherein $R_3$ is phenyl substituted by $-CO-X-R_5$, wherein X is O or NH and $R_5$ is optionally substituted $C_1$-$C_4$-alkyl.

Especially preferred meanings of $R_1$ and $R_1'$ are $-NH-R_3$, wherein $R_3$ is phenyl substituted by $-CO-X-R_5$, wherein X is O or NH and $R_5$ is 2-hydroxyethyl.

In the group $-O-R_4$ the radical $R_4$ is preferably $C_1$-$C_4$-hydroxyalkyl or $C_1$-$C_4$-alkoxy-$C_1$-$C_4$-alkyl. Most preferably $R_4$ is hydroxyethyl, hydroxypropyl, hydroxybutyl or ethoxyethyl.

The novel compounds of formula (1) are a further embodiment of the invention.

Particularly preferred are compounds of the formula (1) wherein $R_1$ and $R_1'$ are identical and are each $-NH-R_3$, $-N(R_3)_2$ or $-O-R_3$, wherein $R_3$ is phenyl substituted by $-CO-X-R_5$, wherein X is O or NH and $R_5$ is optionally substituted $C_1$-$C_4$-alkyl, $R_2$ and $R_2'$ are identical and are each $-O-R_4$, wherein $R_4$ is $C_1$-$C_4$-hydroxyalkyl or $C_1$-$C_4$-alkoxy-$C_1$-$C_4$-alkyl.

The quantities of compound (1) to be applied to the cellulosic material according to the process of the invention may vary over a wide range. However, when used in amounts of between 0.001 and 2% by weight, based on the weight of the fibre material, useful effects may be obtained. Preferably, however, the amount of the compound of formula (1) used is from 0.005 to 1% and especially from 0.01 to 0.5% by weight, based on the weight of the fibre material.

Cellulosic fibre materials are to be understood as meaning, for example, the natural cellulose fibre, such as cotton, linen and hemp, and also cellulose pulp and regenerated cellulose. The process of the invention is also suitable for treating hydroxyl-containing fibres present in blend fabrics, for example, blends of cotton with polyester fibres or polyamide fibres.

The fibre materials used have a density of between 30 and 200 g/m², preferably between 100 and 150 g/m², the porosity of the material lying in the range of 0.1 to 3%, preferably 0.1 to 1.5%.

Preferably, the cellulosic fibre material used is cotton or a cotton blend.

The fibres mentioned may be present in various forms, for example, as staple or yarns or as wovens or knits.

In addition to the compound of formula (1) a UV absorber may also be employed to the cellulosic fibre material. Usually little or no observable reduction of the degrees of whiteness of the so-treated materials results.

For this purpose, application of the UV absorber may be performed before, during or after treatment of the material with the FWA of formula (1).

Any UV absorber suitable for cellulosic fibre materials may be applied for this purpose. The UV absorber used may be, e.g., an o-hydroxybenzophenone, an o-hydroxy-phenylbenzotriazole, a 2-aryl-2H-benzotriazole, a salicylic acid ester, a substituted acrylonitrile, a substituted acrylaminoethylene, a nitrilohydrazone, o-hydroxyaryl-1,3,5-triazine, a sulphonated 1,3,5-triazine or preferably an oxalic anilide.

Preferably reactive UV absorbers are used and particularly preferred are the UV absorbers described in the U.S. Pat. No. 5,700,295, especially the oxalic anilides.

The application of the FWA's and also, when desired, the UV absorbers can take place by an exhaust or continuous process as well known from the literature for similar compounds.

In the exhaust process the liquor ratio can be chosen within a wide range, for example, from 3:1 to 200:1, preferably from 10:1 to 40:1. It is advantageous to operate at a temperature of 20 to 120° C., preferably 40 to 110° C.

The fibre-reactive UV absorbers are applied advantageously in the presence of acid-binding agents, for example, sodium hydroxide, sodium carbonate, sodium bicarbonate, sodium formate, potassium carbonate, sodium silicate, sodium trichloroacetate or sodium triphosphate, in the presence or absence of neutral salts, for example, sodium sulphate or sodium chloride.

The quantities of the UV absorbers to be applied to the cellulosic material according to the process of the invention may vary over a wide range. However, when used in amounts of between 0.005 and 1% by weight, based on the weight of the fibre material, useful effects may be obtained. Preferably, however, the amount of the compound of formula (1) used is from 0.01 to 0.5% by weight, based on the weight of the fibre material.

In the continuous process, the liquor add-on is advantageously 40-700, preferably 40-500, % by weight. The fibre material is then subjected to a heat treatment process to fix the applied FWA's and UV absorbers. This fixing can also be effected by the cold batching method.

The heat treatment preferably takes the form of a steaming process in a steamer with ordinary or superheated steam at a temperature of 98 to 105° C. for, for example, 1-7, preferably 1-5 minutes. The fixing of the UV absorber by the cold batching process can be effected by storing the impregnated and preferably rolled-up material at room temperature (15 to 30° C.) for 3 to 24 hours, for example, the cold batching time being known to depend on the UV absorber.

On completion of the application process and fixation, the treated materials are conventionally rinsed, soaped, for example, for 20 minutes at 90° C. with a solution containing 1 g/l. of calcined sodium carbonate, and dried.

The treatment bath may optionally contain other customary auxiliaries, for example, levelling, wetting deaerating and antifoaming agents, penetration accelerants or crease resisting agents.

The cellulose fibre materials treated by the process of the present invention possess high sun protection factors. The sun protection factor is defined as the ratio of the harmful dose of UV energy on protected skin to the harmful dose of UV energy on unprotected skin. Accordingly, a sun protection factor is also a measure of the transmissivity of fibre materials untreated and of those treated with FWA's and reactive UV absorbers described in this invention.

The sun protection factor can be determined, for example, by the method described by B. L. Diffey and J. Robson in J. Soc. Cosmet. Chem., 40, 127-133 (1989).

The fluorescent whitening agents of formula (1) are new and are a further subject of the present invention.

The invention thus also provides compounds of formula

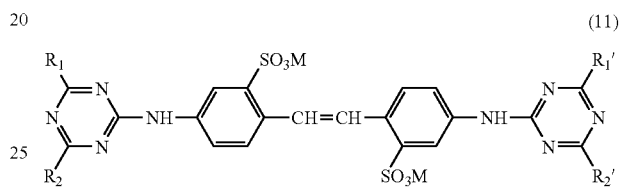

(11)

in which M is hydrogen, an alkali metal atom, ammonium or a cation formed from an amine; $R_1$ and $R_1'$ independently of each other are hydroxy, optionally substituted alkyl, 4-morpholinyl, —NH—$R_3$, —N($R_3$)$_2$ or —O—$R_3$, wherein $R_3$ is optionally substituted alkyl or optionally substituted aryl, $R_2$ is a group of formula —O—$R_4$ wherein $R_4$ is hydroxy alkyl, alkoxy alkyl or hydroxy alkoxy alkyl, and $R_2'$ has the meaning of $R_1$ or $R_2$.

The compounds of formula (1) can be prepared by known methods, e.g., by reacting, under known reaction conditions, cyanuric chloride, successively, in any desired sequence, with each of an aminostilbene-disulfonic acid and compounds capable of introducing the groups $R_1$, $R_1'$, $R_2$ and $R_2'$. If $R_2$ and/or $R_2'$ has the meaning —O—$R_4$ conveniently an alcohol of the formula HO—$R_4$ is used. If this alcohol contains an additional hydroxy residue, usually mixtures of compounds of formula (1) are obtained. The specific composition of those mixtures depends on the reactivity of the different OH-residues of the alcohol. It is, however, usually not necessary to isolate the individual components of such mixtures as all the components exhibit similar advantageous properties as fluorescent whitening agents. If desired, isolation can be afforded by known methods.

The compounds of formula (1) exhibit distinguished solubility in water combined with good affinity to cellulosic fibre material and aqueous formulations containing these compounds have excellent storage stability. They confer to the cellulosic material excellent sun protection and a high degree of whiteness.

The examples which follow illustrate the invention; parts and percentages are by weight unless otherwise stated.

EXAMPLE 1

Preparation of the Compound

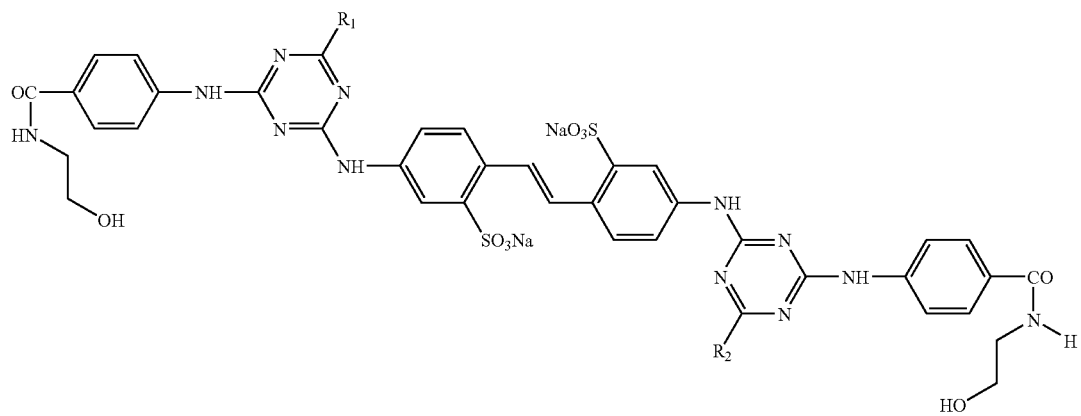

Mixture of the following three compounds:
a) $R_1=R_2=$—O—CH(CH$_3$)—CH$_2$—OH,
b) $R_1=R_2=$—O—CH$_2$—CH(CH$_3$)—OH and
c) $R_1=$—O—CH(CH$_3$)—CH$_2$—OH; $R_2=$—O—CH$_2$—CH(CH$_3$)—OH.

1. Step 214 g water is added to a laboratory reaction flask, followed by 4 g sodium chloride. Contents of the reaction flask are chilled to 10° C. using an ice bath. To the reaction flask is added 15.6 g cyanuric chloride slowly in 10 minutes. After all of the cyanuric chloride is added, a white suspension is formed, pH of the flask contents is 3.10.

To the reaction flask, still at 10° C. is added 140 g of a 12% (wt./vol. 9 solution of 4,4'-diaminiostiblene-2,2'-disulfonic acid sodium salt (DAS) over a 1 hour period. After the addition is complete, the reaction mixture is held for another 50 minutes. The pH increases to 4.42. The pH is controlled between 3 and 4.5 during the reaction using 2.77 g 20% wt./vol. (17% wt./wt.) sodium carbonate. Contents of the flask is light orange in color with the suspension having good stirability. HPLC verifies that the reaction is complete, 96-97% purity.

2. Step

In a laboratory flask is placed 60 g water and 4 g sodium chloride. Then 15.92 g 4-amino-N-(2-hydroxyethyl)-benzamide is added to form a suspension. The suspension is heated to 60° C. with stirring. During 15 minutes the suspension dissolves with the pH being 8.5. The aqueous suspension from the first reaction step, still at 16° C., is added to the aqueous solution of the benzamide over a 30 minute period. After the first 100 ml added, a bright yellow suspension is formed and the agitation is increased to compensate for the viscosity increase. The temperature of the reaction flask is maintained at 60° C. and pH is controlled between 6.5-7.0 using 1 M sodium carbonate. When the addition is complete, the reaction mixture is stirred for another 1 hour at 60° C. HPLC shows that the reaction is complete, 94-95% purity. Temperature of the reaction mixture is increased to 90° C. The viscosity of the reaction mixture increases and the pH drops to 5.32. Then pH is adjusted with 1 M sodium carbonate to 6.0.

3. Step:

To a suspension of 4 g of the second step reaction product in 10 ml propylene glycol are added slowly 1 g 32% wt./vol. NaOH with stirring. The suspension is heated to 90° C. and held at this temperature with stirring for 2 hours. 6 g water is added and the reaction mixture is filtered to give a ca. 20% solution of formula (101).

EXAMPLE 2

Working according to example 1 but substituting in the third step 10 ml propylene glycol with 10 ml 1,2-butylene glycol gives a ca. 20% solution of a mixture of the following three compounds of formula (101):
a) $R_1=R_2=$—O—CH(CH$_2$—CH$_3$)—CH$_2$—OH,
b) $R_1=R_2=$—O—CH$_2$—CH(CH$_2$—CH$_3$)—OH and
c) $R_1=$—O—CH(CH$_2$—CH$_3$)—CH$_2$—OH; $R_2=$—O—CH$_2$—CH(CH$_2$—CH$_3$)—OH.

EXAMPLE 3

Following the procedure of Example 1, but substituting in the third step 10 ml propylene glycol with a mixture of 5 ml propylene glycol and 5 ml 1,2-butylene glycol gives a ca. 20% solution of a mixture of the corresponding compounds of formula (101) containing the propylene glycol and 1,2-butylene glycol bond via oxygen to the triazine rings.

EXAMPLE 4

Following the procedure of Example 1, but substituting in the third step 10 ml propylene glycol with a mixture of 5 ml propylene glycol and 5 ml diehtylene glycol gives a ca. 20% solution of a mixture of the corresponding compounds of formula (101) containing the propylene glycol and diethylene glycol bond via oxygen to the triazine rings.

EXAMPLE 5

Preparation of the Compound

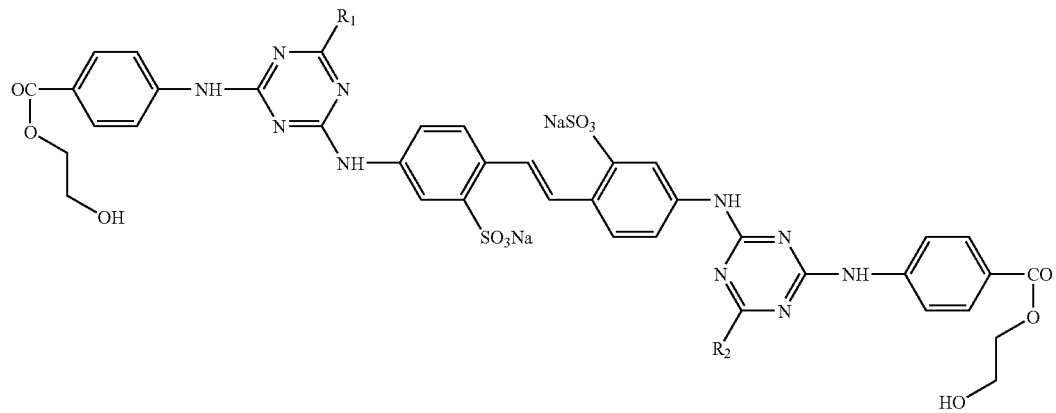
(102)

Mixture of the following three compounds:
a) $R_1=R_2=-O-CH(CH_3)-CH_2-OH$,
b) $R_1=R_2=-O-CH_2-CH(CH_3)-OH$ and
c) $R_1=-O-CH(CH_3)-CH_2-OH$; $R_2=-O-CH_2-CH(CH_3)-OH$.

The above mixture is prepared analogously to Example 1 but replacing in the second step 15.92 g 4-amino-N-(2-hydroxyethyl)-benzamide with equivalent amounts of 4-aminobenzoic acid ethyl ester.

EXAMPLE 6

Two samples each of 10 g of a pre-washed cellulose fabric (cotton cretonne) are treated in an AHIBA® dyeing machine for 60 minutes at 95° C. at a liquor ratio of 1:20 in two different aqueous liquors.
A) 3.0 ml/l hydrogen peroxide 35% 2.0 ml/l sodium silicate 38° Bé2.0 ml/l caustic soda 36° Bé0.5 g/l ULTRAVON EL
B) The same liquor as in A), but containing additionally 0.014% compound of formula (102) according to Example 5.
C) The same liquor as in A), but containing additionally 0.028% compound of formula (102) according to Example 5.
D) The same liquor as in A), but containing additionally 0.015% compound of formula (101) according to Example 4.
E) The same liquor as in A), but containing additionally 0.03% compound of formula (101) according to Example 4.

The results are given in the following table:

| Example | WG (Ganz) * | SPF value ** |
|---|---|---|
| 9 A) | 83 | 3.3 |
| 9 B) | 215 | 16.0 |
| 9 C) | 223 | 21.2 |
| 9 D) | 222 | 20.4 |
| 9 E) | 226 | 24.2 |

\* Whiteness degree: according to Ganz
\*\* Sun Protection Factor (SPF): according to AS/NZS 4399: 1996, Melbourne sunlight (average of 4 measurements)

The above results clearly demonstrate the substantial improvement in sun protection factor attained by the use of compounds of Examples 4 and 5, respectively.

The invention claimed is:

1. A process for improving the sun protection factor (SPF) of cellulosic fibre materials and blends thereof, which comprises contacting said materials with at least one compound of the formula

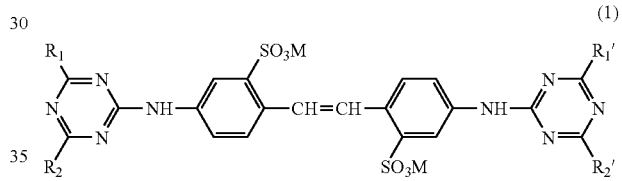
(1)

in which M is hydrogen, an alkali metal atom, ammonium or a cation formed from an amine;
$R_1$ and $R_1'$ independently of each other are $-NH-R_3$, wherein $R_3$ is phenyl substituted by $-CO-X-R_5$, wherein X is O or NH and $R_5$ is 2-hydroxyethyl,
$R_2$ is a group of formula $-O-R_4$ wherein $R_4$ is alkoxy alkyl or hydroxy alkoxy alkyl, and $R_2'$ has the meaning of $R_1$ or $R_2$ and
additionally contacting said materials with at least one UV absorber selected from the group consisting of o-hydroxybenzophenone, o-hydroxyphenylbenzotriazole, 2-aryl-2H-benzotriazole, salicylic acid ester, substituted acrylonitrile, substituted acrylaminoethylene, nitrilohydrazone, o-hydroxyaryl-1,3,5-triazine, sulphonated 1,3, 5-triazine and oxalic anilide UV absorbers and
where the SPF achieved is between 16.0 and 24.2.

2. A process according to claim 1 wherein, in the compound of formula (1), $R_1$ and $R_1'$ are identical.

3. A process according to claim 1, wherein, in the compound of formula (1), $R_2$ and $R_2'$ are identical.

4. A process according to claim 1, wherein, in the compound of formula (1), $R_2$ and $R_2'$ are identical and are each $-O-R_4$, wherein $R_4$ is $C_1$-$C_4$-alkoxy-$C_1$-$C_4$-alkyl.

5. A process according to claim 1, wherein the fibre material is additionally contacted with at least one oxalic anilide UV absorber.

6. A process according to claim 1, wherein the amount of the compound of formula (1) used is from 0.001 to 2% by weight, based on the weight of the fibre material.

7. A process according to claim 6, wherein the amount of the compound of formula (1) used is from 0.005 to 1% by weight, based on the weight of the fibre material.

8. A process according to claim 6, wherein the amount of the compound of formula (1) used is from 0.01 to 0.5% by weight, based on the weight of the fibre material.

9. A process according to claim 1, wherein the cellulosic fibre materials used have a density of between 30 and 200 g/m$^2$.

10. A process according to claim 1, wherein the cellulosic fibre materials used have a porosity of between 0.1 and 3%.

11. A process according to claim 1, wherein the cellulosic fibre material used is cotton or a cotton blend.

12. A process according to claim 1, wherein the cellulosic fibre materials used have a density of between 100 and 150 g/m$^2$.

13. A process according to claim 1, wherein the cellulosic fibre materials used have a porosity of between 0.1 and 1.5%.

* * * * *